United States Patent
Adomat et al.

(10) Patent No.: US 9,693,939 B2
(45) Date of Patent: Jul. 4, 2017

(54) TOOTHPASTE FOR ELECTRIC TOOTHBRUSHES

(71) Applicant: HENKEL AG & CO. KGAA, Dusseldorf (DE)

(72) Inventors: Christel Adomat, Dusseldorf (DE); Nicole Duschek, Dusseldorf (DE); Claudia Hundeiker, Meerbusch (DE)

(73) Assignee: Henkel AG & Co. KGaA, Duesseldorf (DE)

(*) Notice: Subject to any disclaimer, the term of this patent is extended or adjusted under 35 U.S.C. 154(b) by 163 days.

(21) Appl. No.: 14/199,765

(22) Filed: Mar. 6, 2014

(65) Prior Publication Data

US 2014/0182621 A1    Jul. 3, 2014

Related U.S. Application Data

(63) Continuation of application No. PCT/EP2012/065937, filed on Aug. 15, 2012.

(30) Foreign Application Priority Data

Sep. 9, 2011    (DE) .................. 10 2011 082 431

(51) Int. Cl.

| | |
|---|---|
| *A61K 8/26* | (2006.01) |
| *A61K 8/24* | (2006.01) |
| *A61K 8/25* | (2006.01) |
| *A61K 8/44* | (2006.01) |
| *A61K 8/46* | (2006.01) |
| *A61Q 11/00* | (2006.01) |

(52) U.S. Cl.
CPC .................. *A61K 8/26* (2013.01); *A61K 8/24* (2013.01); *A61K 8/25* (2013.01); *A61K 8/44* (2013.01); *A61K 8/463* (2013.01); *A61Q 11/00* (2013.01); *A61K 2800/87* (2013.01)

(58) Field of Classification Search
CPC ...................................................... A61K 33/56
See application file for complete search history.

(56) References Cited

U.S. PATENT DOCUMENTS

| | | |
|---|---|---|
| 3,268,455 A | 8/1966 | Bryce et al. |
| 2004/0131560 A1 | 7/2004 | Corcoran et al. |
| 2006/0222602 A1 | 10/2006 | Barth et al. |
| 2007/0041914 A1 | 2/2007 | Gaffar et al. |
| 2009/0246151 A1 | 10/2009 | LeBlanc et al. |
| 2010/0135921 A1 | 6/2010 | Hughes et al. |
| 2011/0020248 A1 | 1/2011 | Strand |

FOREIGN PATENT DOCUMENTS

| | | |
|---|---|---|
| WO | 01/62210 A2 | 8/2001 |
| WO | 02/26203 A2 | 4/2002 |
| WO | 2008/145475 A1 | 12/2008 |

OTHER PUBLICATIONS

PCT International Search Report (PCT/EP2012/065937) dated Oct. 21, 2013.
German Standard; DIN 53601, "Testing of Carbon Blacks; Determination of the Dibutylphthalate Absorption of Carbon Blacks", pp. 1-3; Dec. 1978.
European Standard, "General methods of test for pigments and extenders; Determination of tamped volume and apparent density after tamping", ISO 787-11:1981; pp. 1-4; Oct. 1995.
International Standard Fourth Addition; ISO 5794-1:2010(E), "Rubber compounding ingredients—Silica, precipitated, hydrated—Part 1: Non-rubber tests", Annex D "Determination of specific surface area", pp. 13-19; Mar. 15, 2010.

*Primary Examiner* — Benjamin Packard
(74) *Attorney, Agent, or Firm* — P. Scott Smith

(57) ABSTRACT

Oral and dental care and cleaning agents are provided for use with an electric toothbrush. The oral and dental care and cleaning agent includes at least one polishing agent and at least one surfactant. A weight ratio of the at least one polishing agent to the at least one surfactant is less than or equal to six.

5 Claims, No Drawings

TOOTHPASTE FOR ELECTRIC TOOTHBRUSHES

RELATED APPLICATIONS

The present specification is a U.S. continuation patent application under 35 U.S.C. 111(a) and claims the right of priority under 35 U.S.C. 365 to international patent Application No. PCT/EP2012/065937, filed Aug. 15, 2012, entitled "SPECIAL TOOTHPASTE FOR ELECTRIC TOOTH BRUSHES I" which claims benefit of German application No.: 102011082431.6, filed Sep. 9, 2011, these applications are herein incorporated by reference in their entirety.

FIELD OF THE INVENTION

The present invention generally relates to a dentifrice (i.e., a toothpaste) that takes into account the particular requirements associated with the use of electric toothbrushes.

BACKGROUND OF THE INVENTION

Dental cleaning agents are on the market in a variety of forms, and are used to clean the tooth surface and to prevent diseases of the teeth and gums. They may contain a combination of polishing agents, humectants, surfactants, binding agents, flavorings, and fluoride-containing and antimicrobial active agents. Besides tooth powders, which play a subordinate role because of their elevated abrasiveness, dental cleaning agents are offered principally in the form of a paste, cream, translucent gel, or transparent gel. Liquid dentifrices and mouthwashes have also become increasingly significant in recent years.

Developments have also been pursued in terms of equipment. Besides the conventional manual toothbrush, which the consumer moves in the mouth using circular motions; electric toothbrushes have also become established on the market. Electric toothbrushes generate some of the motion of the bristles on the tooth surface by means of a battery (usually rechargeable) in a hand piece of the toothbrush. Accordingly, the consumer may, depending on the model, replace the circular hand motion with a horizontal linear motion.

Electric toothbrush heads are common on the market in a variety of configurations. For example, round brush heads are electrically rotated or partly rotated, with clockwise and counterclockwise rotations. Elongated brush heads modeled on conventional toothbrushes may be electrically oscillated.

Electric toothbrushes may relieve the consumer of some of the specific motion sequences used to clean the teeth. These advantages are also accompanied, however, by disadvantages. For example, an electric toothbrush usually exerts a more intense load on the tooth surface than in the case of manual toothbrushing. If the nature and concentration of the abrasive materials in the dentifrice are not coordinated with this load, damage to the tooth enamel may occur in connection with electric toothbrush use.

A further problem is the fact that the complex mechanism in the toothbrush may become clogged, and the toothbrush may not allow movement of the brush head. Additional attention is also given to rheology, since a dentifrice should adhere to the electric toothbrush head in order to prevent the dentifrice from spraying.

Some of the aforementioned requirements are mutually contradictory, since abrasive materials are at least in part also consistency agents.

Accordingly, the present systems and methods provide an oral and dental care and cleaning agent that is suitable specifically for electric toothbrushes and that overcomes the disadvantages recited above. More specifically, the present systems and methods achieve a high level of cleaning performance without excessive abrasiveness. The present systems and methods allow for low stress on the sensitive mechanism of the electrically operated brush heads and sufficient adhesion to the brush head.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An oral and dental care and cleaning agent containing at least one polishing agent and at least one surfactant, characterized in that the weight ratio of polishing agent(s) to surfactant(s) is less than or equal to 6.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

According to the present specification polishing agents and surfactants may be used within different ratios with respect to one another in order to overcome the disadvantages mentioned above.

In a first example, the present specification describes an oral and dental care and cleaning agent including: at least one polishing agent and at least one surfactant. The weight ratio of the polishing agents to surfactants is less than or equal to six.

As used in the present specification and in the appended claims, the phrases "oral and dental care agents," "oral and dental cleaning agents," "oral care agents," "dental care agents" or similar terminology may refer to oral and dental powders, oral and dental pastes, liquid oral and dental creams, oral and dental rinses, and oral and dental gels. Toothpastes and liquid dental cleaning agents are preferably suitable. The oral care agents may be in the form of toothpastes, liquid dentifrices, tooth powders, mouthwashes, or a chewing compound, e.g. as chewing gum. In some examples, the oral care agent may be a flowable or plastic toothpaste, such as those used to clean teeth using a toothbrush. Other examples of oral care agents include oral rinse solutions and mouthwashes that are used to rinse out the oral cavity.

The oral and dental care and cleaning agents may contain at least one polishing agent. Examples of polishing agents are, in principle, friction bodies used in a toothpaste, in particular those that contain no calcium ions. Preferably suitable polishing agent components may be silicic acids, aluminum hydroxide, aluminum oxide, sodium aluminum silicates, organic polymers, or mixtures of such friction bodies.

Calcium-containing polishing components, for example chalk, calcium pyrophosphate, dicalcium phosphate dihydrate may be contained in quantities of up to 5 wt %, based on the total composition.

The total polishing agent content may be preferably in the range from 5 to 50 wt % of the oral and dental care and cleaning agent. Preferred, oral and dental care and cleaning agents may contain polishing agents within narrower quantity ranges. Preferred oral and dental care and cleaning agents may be characterized here in that they contain, based on their weight, 1 to 25 wt %, preferably 2.5 to 20 wt %, more preferably 5 to 18 wt %, and in particular 7.5 to 16 wt % polishing agent(s).

Toothpastes and liquid dental cleaning agents may include silicic acids as polishing agent(s) are particularly preferred. Examples of silicic acids include silicic acid gels, silicic acid hydrogels, and precipitated silicic acids. Silicic acid gels may be manufactured by reacting sodium silicate solutions with strong aqueous mineral acids to form a hydrosol, aging to a hydrogel, washing, and drying. If drying occurs under mild conditions to water contents from 15 to 35 wt %, so-called silicic acid hydrogels may be obtained. Drying to water contents below 15 wt % results in an irreversible shrinkage of the previously loose structure of the hydrogel to the dense structure of the so-called xerogel.

A second preferably suitable group of silicic acid polishing agents is the precipitated silicic acids. These may be obtained by precipitating silicic acid from dilute alkali silicate solutions by adding strong acids under conditions in which aggregation to a sol and gel cannot occur. A precipitated silicic acid having a BET surface area from 15 to 110 $m^2/g$, a particle size from 0.5 to 20 µm, where at least 80 wt % of the primary particles are to be below 5 µm, and a viscosity in a 30% glycerol/water dispersion (1:1) from 30 to 60 Pa·s (20° C.), is preferably suitable, in a quantity from 10 to 20 wt % of the toothpaste. Preferably suitable precipitated silicic acids of this kind may exhibit rounded corners and edges, and may be obtainable under the commercial name Sident® 12 DS (DEGUSSA).

Other precipitated silicic acids of this kind may be obtained under the commercial name Sident® 8 (DEGUSSA) and Sorbosil® AC 39 (Crosfield Chemicals). These silicic acids may include a reduced thickening effect and may have an average particle size of 8 to 14 µm with a specific surface area from 40 to 75 $m^2/g$ (according to BET), and are particularly suitable for liquid dentifrices. These may have a viscosity (25° C., shear rate $D=10\ s^{-2}$) from 10 to 100 Pas.

On the other hand, toothpastes that have an appreciably higher viscosity of more than 100 Pas (25° C., $D=10\ s^{-1}$) may include silicic acids having a particle size less than 5 µm, preferably at least 3 wt % of a silicic acid having a particle size from 1 to 3 µm. Even finer-particulate so-called "thickening" silicic acids having a BET surface area from 150 to 250 $m^2/g$, for example the commercial products Sipernat 22 LS or Sipernat® 320 DS may be added to such toothpastes in addition to the aforesaid precipitated silicic acids.

Oral and dental care and cleaning agents may include polishing-agent components that can be contained such as, for example, aluminum oxide in the form of low-calcined alumina having an α- and β-aluminum oxide content, in a quantity of approx. 1 to 5 wt %. A suitable aluminum oxide of this kind is obtainable under the commercial name "ultrafine polishing alumina P10" (Giulini Chemie).

Also suitable as polishing agents are friction bodies such as sodium aluminum silicates such as e.g. zeolite A, organic polymers such as e.g. polymethacrylate, or mixtures of these and the previously mentioned friction bodies.

Oral and dental care and cleaning agents according to the present specification may additionally contain cleaning bodies, preferably silicic acids, aluminum hydroxide, aluminum oxide, calcium pyrophosphate, chalk, dicalcium phosphate dihydrate ($CaHPO_4.2H_2O$), sodium aluminum silicates, in particular zeolite A, organic polymers, in particular polymethacrylates, or mixtures of said friction bodies, preferably in quantities from 1 to 30 wt %, preferably from 2.5 to 25 wt %, and in particular from 5 to 22 wt %, based in each case on the total agent, are preferred.

Oral and dental care and cleaning agents particularly preferred may contain exclusively polishing agents from the group of silicic acids, aluminum hydroxide, aluminum oxide, dicalcium phosphate dihydrate ($CaHPO_4.2H_2O$), or mixtures of said friction bodies. These polishing agents may be particularly efficient.

Very particularly preferably, the compositions according to the present specification may contain, based on their weight, 1 to 30 wt % of precipitated silicic acid(s) having a specific surface area ≤55 $m^2/g$ according to ISO 5794-1. The precipitated silicic acids that exhibit corresponding specific surface areas are preferably used within narrower quantity ranges; particularly preferably, precipitated silicic acids that have even lower specific surface areas according to ISO 5794-1. Preferred oral and dental care and cleaning agents according to the present specification may contain 2.5 to 25 wt %, preferably 5 to 20 wt %, particularly preferably 7.5 to 17.5 wt %, more preferably 8.0 to 15.0 wt %, and in particular 10.0 to 13.0 wt % precipitated silicic acid(s) having a specific surface area ≤55 $m^2/g$ according to ISO 5794-1.

Particularly preferred oral and dental care and cleaning agents may be characterized in that all precipitated silicic acid(s) contained in the agent have a specific surface area ≤53 $m^2/g$, preferably ≤51 $m^2/g$, more preferably ≤49 $m^2/g$, and in particular ≤47 $m^2/g$ according to ISO 5794-1.

In further preferred agents the precipitated silicic acids used may be characterized by further physical parameters. Precipitated silicic acids that are preferably to be used have tamped densities >360 g/l (measured according to ISO 787-11), particularly preferably >375 g/l, more preferably >400 g/l, and in particular >425 g/l.

It is further preferred to employ precipitated silicic acids that have a DBP absorption according to DIN 53601 of less than 140 g/100 g. Very particularly preferred precipitated silicic acids to be used according to the present invention have a DBP absorption according to DIN 53601 of less than 135 g/100 g, preferably a DBP absorption according to DIN 53601 of less than 130 g/100 g, and in particular less than 125 g/100 g.

Agents particularly preferred may contain 2.5 to 25 wt %, preferably 5 to 20 wt %, particularly preferably 7.5 to 17.5 wt %, more preferably 8.0 to 15.0 wt %, and in particular 10.0 to 14.0 wt % precipitated silicic acid(s) having a specific surface area ≤45 $m^2/g$ according to ISO 5794-1 and a tamped density >425 g/l (measured according to ISO 787-11).

Agents further preferred may contain 2.5 to 25 wt %, preferably 5 to 20 wt %, particularly preferably 7.5 to 17.5 wt %, more preferably 8.0 to 15.0 wt %, and in particular 10.0 to 14.0 wt % precipitated silicic acid(s) having a specific surface area ≤45 $m^2/g$ according to ISO 5794-1 and a DBP absorption according to DIN 53601 of less than 125 g/100 g.

Agents particularly preferred may contain 2.5 to 25 wt %, preferably 5 to 20 wt %, particularly preferably 7.5 to 17.5 wt %, more preferably 8.0 to 15.0 wt %, and in particular 10.0 to 14.0 wt % precipitated silicic acid(s) having a specific surface area ≤45 $m^2/g$ according to ISO 5794-1 and a tamped density >425 g/l (measured according to ISO 787-11) and a DBP absorption according to DIN 53601 of less than 125 g/100 g.

The oral and dental care and cleaning agents may include a surfactant. The surfactants as well are preferably used within narrow quantity ranges, so that preferred oral and dental care and cleaning agents may be characterized in that they contain, based on their weight, 0.5 to 5 wt %, preferably 0.75 to 4.5 wt %, more preferably 1 to 4 wt %, even more preferably 1.25 to 3.5 wt %, and in particular 1.6 to 2.5 wt % surfactant(s).

Examples of surfactants include linear sodium alkyl sulfates having 12 to 18 carbon atoms in the alkyl group. These substances have an enzyme-inhibiting effect on the bacterial metabolism of dental plaque. Other examples of surfactants may include alkali salts, preferably sodium salts, of alkyl polyglycol ether sulfate having 12 to 16 carbon atoms in the linear alkyl group and 2 to 6 glycol ether groups in the molecule, of linear alkane ($C_{12}$ to $C_{18}$)-sulfonate, of sulfosuccinic acid monoalkyl ($C_{12}$ to $C_{18}$) esters, of sulfatized fatty acid monoglycerides, sulfatized fatty acid alkanolamides, sulfoacetic acid alkyl ($C_{12}$ to $C_{18}$) esters, acyl sarcosines, acyl taurides, and acyl isethionates each having 8 to 18 carbon atoms in the acyl group. Zwitterionic, ampholytic, and nonionic surfactants are also suitable, e.g. oxethylates of fatty acid mono- and diglycerides, of fatty acid sorbitan esters, and alkyl(oligo)-glucosides.

In some examples, the preferred surfactants used in an oral and dental care and cleaning agent may be anionic surfactants. A preferred oral and dental care and cleaning agent may be characterized in that it contains, based on weight, 0.25 to 4 wt %, preferably 0.5 to 3.5 wt %, more preferably 0.75 to 3 wt %, even more preferably 1 to 2.5 wt %, and in particular 1.6 to 2.2 wt % anionic surfactant(s).

Examples of anionic surfactants may include soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ethercarboxylic acids and salts thereof, fatty acid isethionates, fatty acid sarcosinates, fatty acid taurides, N-acylamino acids, for example acyl lactylates, acyl tartrates, acyl glutamates, and acyl aspartates, alkyl oligoglucoside sulfates, protein fatty acid condensates (in particular wheat-based plant products), alkyl (ether) phosphates, or combinations thereof. If the anionic surfactants contain polyglycol ether chains, they may exhibit a conventional or a restricted homolog distribution.

Very particularly preferred oral and dental care and cleaning agents may also include an alkyl sulfate(s) as an anionic surfactant. More specifically, preferred oral and dental care and cleaning agents may include 0.25 to 4 wt %, preferably 0.5 to 3.5 wt %, more preferably 0.75 to 3 wt %, even more preferably 1 to 2.5 wt %, and in particular 1.6 to 2.2 wt % sodium dodecyl sulfate.

With particular preference, the oral and dental care and cleaning agents may contain amphoteric surfactant(s). "Amphoteric" surfactants and emulsifier agents may refer to those surface-active compounds that contain, a $C_8$ to $C_{24}$ alkyl or acyl group, at least one free amino group and at least one —COOH or —$SO_3H$ group, and are capable of forming internal salts. Examples of amphoteric surfactants may include N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids, having in each case approximately 8 to 24 carbon atoms in the alkyl group. Examples of amphoteric surfactants are N-cocalkylaminopropionate, cocacylaminoethylaminopropionate, and $C_{12}$ to $C_{18}$ acyl sarcosine.

Particularly preferred oral and dental care and cleaning agents may include 0.01 to 2 wt %, preferably 0.05 to 1.5 wt %, more preferably 0.1 to 1 wt %, even more preferably 0.12 to 0.7 wt %, and in particular 0.15 to 0.6 wt % amphoteric surfactant(s).

Particularly preferred oral and dental care and cleaning agents according to the present invention are characterized in that they contain amphoteric surfactant(s) from the groups of: eN-alkylglycines, N-alkylpropionic acids, N-alkylaminobutyric acids, N-alkyliminodipropionic acids, N-hydroxyethyl-N-alkylamidopropyl glycines, N-alkyltaurines, N-alkylsarcosines, 2-alkylaminopropionic acids each having approximately 8 to 24 carbon atoms in the alkyl group, alkylaminoacetic acids each having approximately 8 to 24 carbon atoms in the alkyl group, N-cocalkylamninopropionate, cocacylaminoethylaminopropionate, $C_{12}$ to $C_{18}$ acyl sarcosine, N-alkyl-N,N-dimethylammonium glycinates, for example cocalkyldimethylammonium glycinate, N-acylaminopropyl-N,N-dimethylammonium glycinates, for example cocacylaminopropyldimethylammonium glycinate, 2-alkyl-3-carboxymethyl-3-hydroxyethylimidazolines each having 8 to 18 carbon atoms in the alkyl or acyl group, cocacylaminoethylhydroxyethylcarboxymethyl glycinate, the compounds known by the INCI name Cocamidopropyl Betaine, the compounds known by the INCI name Disodium Cocamphodiacetate.

Particularly preferred oral and dental care and cleaning agents may include, as amphoteric surfactants, betaines of formula (Bet-I)

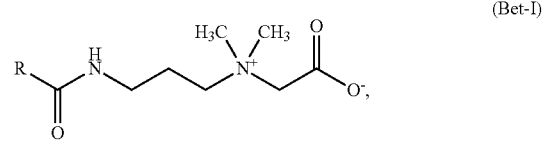

(Bet-I)

in which R denotes a straight-chain or branched, saturated or mono- or poly-unsaturated alkyl or alkenyl residue, respectively, having 8 to 24 carbon atoms.

These surfactants may be referred to according to INCI nomenclature as Amidopropyl Betaines; the representatives that derive from coconut fatty acids are preferred, and may be referred to as Cocamidopropyl Betaines. It is particularly preferred according to the present invention to use surfactants of formula (Bet-I) that are a mixture of the following representatives:

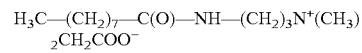

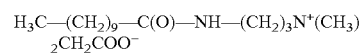

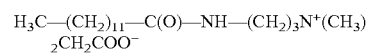

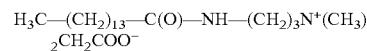

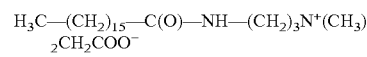

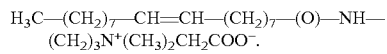

Particularly preferably, surfactants of formula (Bet-I) are used within narrower quantitative ranges. Preferred in this context are oral and dental care and cleaning agents that contain, based on their weight, 0.01 to 2 wt %, preferably 0.05 to 1.5 wt %, more preferably 0.1 to 1 wt %, even more preferably 0.12 to 0.7 wt %, and in particular 0.15 to 0.6 wt % Cocamidopropyl Betaine.

The weight ratio of polishing agent(s) to surfactant(s) may be less than or equal to 6, i.e. the polishing agents may be used at most at a sixfold (weight) excess in terms of the surfactants. The "weight ratio" may refer to the weight ratio of all substances from the groups recited, or to the weight ratio of the active substances being calculated. For example, if an agent contains 12 wt % polishing agent and 4 wt % of a 50% surfactant solution, the weight ratio is then 12/2=6. If an agent according to the present invention contains, for example, 12 wt % polishing agent and 4 wt % of a 50% surfactant solution as well as 1 wt % pure sodium dodecyl sulfate, the weight ratio is then 12/(2+1)=4.

In preferred agents the weight ratio falls within an even narrower range. Particularly preferred oral and dental care and cleaning agents are characterized in that the weight ratio of polishing agent(s) to surfactant(s) is in the range of ≥4 to ≤5.9, preferably in the range of ≥4.5 to ≤5.8, more preferably in the range of ≥5 to ≤5.7, and in particular in the range of ≥5.25 to ≤5.6.

Oral and dental care and cleaning agents, in particular toothpastes, can also contain, for example, substances that are effective against plaque and/or tartar.

Plaque is a coarse, sticky coating on the teeth that is made up of saliva, bacteria, and food residues. If mineral salts (e.g. calcium, phosphates) from saliva become deposited in the plaque, this causes the formation of hard white or yellowish deposits on the teeth called "tartar." Plaque can in turn easily become deposited in the porous tartar and attack the gums.

Bacteria on the tooth surface break down carbohydrates from food, particularly sugar, into acid. This acid dissolves the tooth substance, and caries (cavities) occur. The minerals calcium and phosphate are, in particular, dissolved out of the enamel. After the enamel coating, internal layers of the tooth are also attacked. Bacteria can penetrate into the tooth pulp and cause inflammation there. This then usually causes intense toothache.

As already mentioned, plaque contains bacteria, so that antimicrobial substances are suitable for counteracting plaque. They furthermore have an effect as preservatives.

The preservatives sorbic acid (E 200), potassium sorbate (E 202), calcium sorbate (E 203), benzoic acid (E 210), sodium benzoate (E 211), potassium benzoate (E 212), calcium benzoate (E 213), ethyl-4-hydroxybenzoate (E 214), ethyl-4-hydroxybenzoate, sodium salt (E 215), propyl-4-hydroxybenzoate (E 216), propyl-4-hydroxybenzoate, sodium salt (E 217), methyl-4-hydroxybenzoate (E 218), methyl-4-hydroxybenzoate, sodium salt (E 219), sulfur dioxide (sulfurous acid), (E 220), sodium sulfite (E 221), sodium hydrogen sulfite (E 222), sodium disulfite (E 223), potassium disulfite (E 224), calcium sulfite (E 226), calcium hydrogen sulfite (E 227), potassium hydrogen sulfite (E 228), biphenyl (E 230), orthophenylphenol (2-biphenylol), (E 231), sodium orthophenyl phenolate (E 232), Nisin (E 234), natamycin (E 235), formic acid (E 236), sodium formate (E 237), calcium formate (E 238), hexamethylenetetramine (E 239), dimethyl dicarbonate (E 242), potassium nitrite (E 249), sodium nitrite (E 250), sodium nitrate (E 251), acetic acid (E 260), potassium acetate (E 261), sodium acetate (E 262), calcium acetate (E 263), lactic acid (E 270), propionic acid (E 280), sodium propionate (E 281), calcium propionate (E 282), potassium propionate (E 283), boric acid (E 284), sodium tetraborate (E 285), hydroxysuccinic acid (malic acid), (E 296), fumaric acid (E 297), lysozyme (E 1105), which are also permitted in food, can be employed, for example, in oral and dental care and cleaning agents.

Preferred substances may be selected from alkylpyridinium salts, in particular cetylpyridinium chloride, p-hydroxybenzoic acid methyl, ethyl, or propyl esters, sodium sorbate, sodium benzoate, bromochlorophen, triclosan, phenyl salicylic acid esters, biguanides, e.g. chlorhexidine (1,1'-hexamethylene bis-[5-(4-chlorophenyl)]biguanide), thymol, etc.

Oral and dental care and cleaning agents preferred may be characterized in that that they additionally contain anti-plaque active agents, preferably alkylpyridinium salts, in particular cetylpyridinium chloride, p-hydroxybenzoic acid methyl, ethyl, or propyl esters, sodium sorbate, sodium benzoate, bromochlorophen, triclosan, hexetidine, phenyl salicylic acid esters, biguanides, e.g. chlorhexidine, thymol, preferably in quantities from 0.05 to 5 wt %, preferably from 0.10 to 2.5 wt %, and in particular from 0.30 to 1.5 wt %, based in each case on the total agent.

The quantities indicated refer to the total quantity of anti-plaque active agents, individual active agents preferably being employed in narrower quantity ranges, Preferred agents may contain, for example, 0.1 to 2 wt %, preferably 0.2 to 1.75 wt %, more preferably 0.3 to 1.5 wt %, and in particular 0.4 to 1.0 wt % sodium benzoate. Agents further preferred may also be characterized in that they contain 0.005 to 0.1 wt %, preferably 0.01 to 0.075 wt %, and in particular 0.02 to 0.05 wt % chlorhexidine. Chlorhexidine is preferably used together with alkylpolyglycosides (APG); alkylglycosides having 8 to 18 carbon atoms in the alkyl group and an average degree of oligomerization of the glycoside residue from 1 to 3 are contained in a quantity from 0.025 to 2.5 wt % in preferred oral and dental care and cleaning agents.

Substances effective against tartar can be, for example, chelating agents such as e.g. ethylenediaminetetraacetic acid and sodium salts thereof, pyrophosphate salts such as water-soluble dialkali or tetraalkali metal pyrophosphate salts, e.g. $Na_4P_2O_7$, $K_4P_2O_7$, $Na_2K_2P_2O_7$, $Na_2H_2P_2O_7$, and $K_2H_2P_2O_7$, or polyphosphate salts that can be selected, for example, from water-soluble alkali metal tripolyphosphates such as sodium tripolyphosphate and potassium tripolyphosphate.

Preferred oral and dental care and cleaning agents may be characterized in that they additionally contain phosphate(s), preferably alkali metal phosphate(s), and in particular sodium tripolyphosphate, preferably in quantities from 1 to 10 wt %, particularly preferably from 2 to 8 wt %, and in particular from 3 to 7 wt %, based in each case on the total agent.

Natural and/or synthetic water-soluble polymers such as alginates, carrageenates, tragacanth, starch and starch ethers, cellulose ethers such as carboxymethyl cellulose (sodium salt), hydroxyethyl cellulose, methylhydroxypropyl cellulose, guar, acacia gum, agar-agar, xanthan gum, succinoglycan gum, locust bean flour, pectins, water-soluble carboxyvinyl polymers (e.g. Carbopor® grades), polyvinyl alcohol, polyvinylpyrrolidone, polyethylene glycols, in particular those having molecular weights from 1500 to 1,000,000, serve, for example, as consistency regulators (respectively binding agents).

Further substances that are suitable for viscosity control are, for example, sheet silicates such as montmorillonite clays, colloidal thickening silicic acids such as aerogel silicic acids, pyrogenic silicic acids, or ultra-finely ground precipitated silicic acids. Viscosity-stabilizing additives from the group of cationic, zwitterionic, or ampholytic nitrogen-containing surfactants, hydroxypropyl-substituted hydrocolloids, or polyethylene glycol/polypropylene glycol copolymers having an average molecular weight from 1000 to 5000, or a combination of the aforesaid compounds, can also be used in toothpastes.

The agents, in particular toothpastes, may also contain substances to increase mineralizing potential, for example calcium-containing substances such as calcium chloride, calcium acetate, and dicalcium phosphate dihydrate. The concentration of calcium-containing substance depends on the solubility of the substance and on the interaction with other substances contained in the oral and dental care agent.

Besides the components recited, the oral and dental care and cleaning agents may contain further adjuvants and additives. One additive that is as a toothpaste component which is particularly effective in the dental care agents of the present disclosure is calcium glycerophosphate, which is the calcium salt of glycerol-1-phosphoric acid or of glycerol-2-phosphoric acid or of glycerol-3-phosphoric acid that is enantiomeric to glycerol-1-phosphoric acid, or of a mixture of said acids. The compound has a remineralizing effect in the oral and dental care and cleaning agents, since it supplies both calcium ions and phosphate ions. Calcium glycerophosphate is contained in the oral and dental care and cleaning agents preferably in quantities from 0.01 to 1 wt %. The oral and dental care and cleaning agents may contain adjuvants and additives in quantities in total of up to 10 wt %.

Oral and dental care and cleaning agents may, with particular preference, contain anti-caries active agents. These may be selected, for example, from organic or inorganic fluorides, e.g. from sodium fluoride, potassium fluoride, sodium monofluorophosphate, and sodium fluorosilicate. Zinc fluoride and tin(II) fluoride are also preferred. A quantity from 0.01 to 0.2 wt % fluoride, in the form of the aforesaid compounds, should preferably be contained.

Oral and dental care and cleaning agents may additionally contain anti-caries active agents, preferably fluorine compound(s), in particular sodium fluoride, potassium fluoride, sodium monofluorophosphate, zinc fluoride, tin fluoride, and sodium fluorosilicate, preferably in quantities from 0.01 to 5 wt %, preferably from 0.1 to 2.5 wt %, and in particular from 0.2 to 1.1 wt %, based in each case on the total agent, are preferred according to the present invention.

The dental care agents may be improved in terms of their organoleptic properties, for example, by adding flavor oils and sweetening agents.

All natural and synthetic flavors usual for oral and dental care agents can be used as flavor oils. Natural flavors can be contained both in the form of natural essential oils isolated from botanicals, and as the individual components isolated therefrom.

Suitable flavors are, for example, peppermint oil, spearmint oil, eucalyptus oil, anise oil, fennel oil, caraway oil, menthyl acetate, cinnamaldehyde, anethol, vanillin, thymol, and mixtures of said components.

Suitable sweetening agents are, for example, sodium saccharin, sodium cyclamate, sucrose, lactose, Meltose, fructose, as well as maltose and dextrose.

A further subject of the present disclosure is the use of agents for cleaning teeth by means of electric toothbrushes.

A further subject of the present disclosure is a method for cleaning teeth, characterized in that an agent is applied onto the brush head of an electric toothbrush and the teeth are brushed with the electric toothbrush.

A further subject is a method for tooth cleaning, characterized by the steps of
a) providing a toothbrush whose brush head can be set in motion electrically,
b) applying 0.5 to 5 g of an agent onto the brush head,
c) brushing teeth for 30 to 300 seconds with the agent, employing the brush head set in motion electrically.

The statements made regarding the agents according to the present disclosure apply mutatis mutandis with respect to preferred examples of the use according to the present disclosure and of the methods according to the present disclosure.

While at least one example has been presented in the foregoing detailed description, it should be appreciated that a vast number of variations exist. It should also be appreciated that the example or examples are only examples, and are not intended to limit the scope, applicability, or configuration of the specification in any way. Rather, the foregoing detailed description will provide those skilled in the art with a convenient road map for implementing an example of the present specification, it being understood that various changes may be made in the function and arrangement of elements described in an example without departing from the scope of the specification as set forth in the appended claims and their legal equivalents.

What is claimed is:

1. An oral and dental care and cleaning agent comprising:
   5 to 18 wt % of at least one polishing agent based on the total weight of the cleaning agent; and
   1.6 to 2.2 weight percent of at least one surfactant based on the total weight of the cleaning agent, wherein the surfactant is an anionic surfactant;
   in which a weight ratio of the at least one polishing agent to the at least one surfactant is ≥5.25 to ≤5.6.

2. The oral and dental care and cleaning agent of claim 1, in which the at least one polishing agent comprises silicic acid, aluminum hydroxide, aluminum oxide, dicalcium phosphate dihydrate ($CaHPO_4.2H_2O$), or combinations thereof.

3. The oral and dental care and cleaning agent of claim 1, in which the oral and dental care and cleaning agent is configured for cleaning teeth by means of electric toothbrushes.

4. A method for cleaning teeth, the method comprising:
   Applying an oral and dental care and cleaning agent onto a brush head of an electric toothbrush, in which the oral and dental care and cleaning agent comprises:
   5 to 18 wt % of at least one polishing agent based on the total weight of the cleaning agent; and
   1.6 to 2.2 weight percent of at least one surfactant based on the total weight of the cleaning agent, wherein the surfactant is an anionic surfactant;
   in which a weight ratio of the at least one polishing agent to the at least one surfactant is ≥5.25 to ≤5.6; and
   brushing the teeth with the electric toothbrush.

5. A method for cleaning teeth, the method comprising:
   providing a toothbrush whose brush head can be set in motion electrically;
   applying 0.5 to 5 g of an agent onto the brush head, in which the cleaning agent comprises:
   5 to 18 wt % of at least one polishing agent based on the total weight of the agent; and 1.6 to 2.2 weight percent of at least one surfactant based on the total weight of the cleaning agent, wherein the surfactant is an anionic surfactant; and
wherein a weight ratio of the at least one polishing agent to the at least one surfactant is ≥5.25 to ≤5.6; and
brushing the teeth for 30 to 300 seconds with the agent.

* * * * *